United States Patent [19]

Sugaya

[11] Patent Number: 4,766,714
[45] Date of Patent: Aug. 30, 1988

[54] APPARATUS FOR LOADING ANALYTICAL SLIDES IN CARTRIDGE

[75] Inventor: Fumio Sugaya, Saitama, Japan

[73] Assignee: Fuji Photo Film Co., Ltd., Kanagawa, Japan

[21] Appl. No.: 39,268

[22] Filed: Apr. 17, 1987

[30] Foreign Application Priority Data

Apr. 19, 1986 [JP] Japan .................................. 61-91024

[51] Int. Cl.$^4$ ............................ B65B 5/08; B65B 5/10
[52] U.S. Cl. ........................................ 53/242; 53/531; 53/390
[58] Field of Search .......................... 53/242, 390, 531; 414/92, 96

[56] References Cited

U.S. PATENT DOCUMENTS 3,547,280 12/1970 Giegerich ............................ 414/92
4,068,767 1/1978 Tippetts ............................... 414/92

Primary Examiner—Horace M. Culver
Attorney, Agent, or Firm—Sughrue, Mion, Zinn, Macpeak and Seas

[57] ABSTRACT

An apparatus for loading analytical slides in a cartridge comprising a tray on which inclined partition members having a width narrower than the width of the analytical slides are provided so as to form a row and a pushing out member which slides on said tray and engages the lower edge of the exposed portion of each analytical slide and push the slides out of said row of partition members into a receiver to stack the analytical slides pushed out from said tray.

13 Claims, 3 Drawing Sheets ns in Cartridge

APPARATUS FOR LOADING ANALYTICAL SLIDES IN CARTRIDGE

BACKGROUND OF THE INVENTION

1. Field of the Invention

This invention relates to an apparatus for loading analytical slides for determining various components of a body fluid such as blood or urine in a cartridge.

2. Description of Prior Art

Recently, in clinical test field, advantages of dry method in simplicity and rapidity have been appreciated, and this method has widely been utilized. In this dry method, a liquid sample such as serum is spotted on an analytical slide containing reagents reacting with the object component of the sample to form color, and content of the object component is colorimetrically determined.

The dry method is usually carried out by using an analyzer in order to secure accurate measurement and simplicity. The analyzer is generally composed of a slide supplying part, a sample spotting part, an incubator and a photometric part. In the slide supplying part, analytical slides arranged in a cartridge are delivered intermittently, and each liquid sample is spotted on the analytical slide delivered from the slide supplying part. The analytical slide is then warmed in the incubator to proceed color reaction of the analyte, and color formed is detected at the photometric part.

The above conventional cartridge was in a box shape of which one face was opened, and each analytical slide was stacked up in the cartridge by hand.

Meanwhile, the above analyzer can measure many components such as glucose, urea nitrogen and hemoglobin by using various analytical slides corresponding to the object component. Then, various analytical slides according to analytical items are combined into a set, and the analytical slides are stacked up in the order of each set. A divider on which a sample number is indicated is interposed between neighboring sets of the analytical slides.

In such a manner, since only one analytical slide stacked just before can be seen by a worker, the worker sometimes misunderstood the stacking order and he set analytical slides erroneously. Moreover, he can not check the stacked order of analytical slides, and accordingly, he could not find the erroneous stacking.

SUMMARY OF THE INVENTION

An object of the invention is to provide an apparatus for loading analytical slide in a cartridge which can correctly load analytical slides in a prescribed order.

Another object of the invention is to provide an apparatus for loading analytical slides in a cartridge which can load analytical slide easily and rapidly.

The present invention provides an apparatus which suits such objects, comprising a tray on which inclined partition members having a width narrower than the width of the analytical slide are provided so as to form a ro and a pushing out member which slides on the above tray and pushes the lower edge of the exposed position of the analytical slide out of the above row of the partition members and which receives to stack the analytical slide pushed out from the tray.

DETAILED DESCRIPTION OF THE INVENTION

Figure 1:
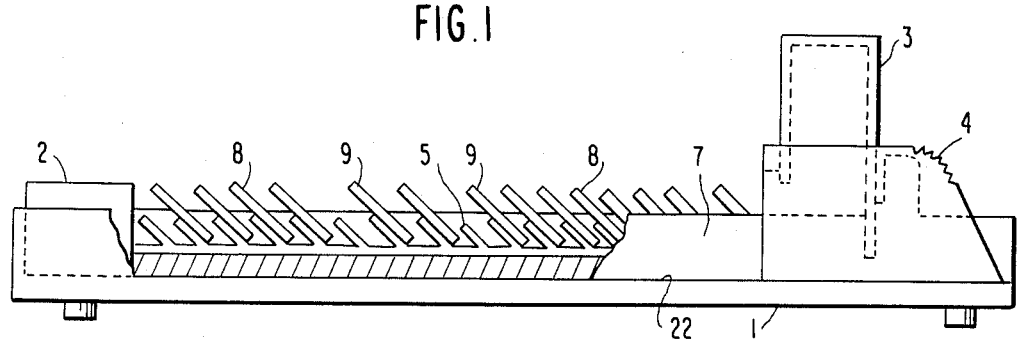
FIG. 1 is a partial cutaway side view of an apparatus for loading analytical slides embodying the invention.

Width of the partition member is made narrower than the width of the analytical slide. By this constitution, a part of the analytical slide is put out of the partition member, and the pushing out member can push the lower edge of the exposed position of the analytical slide. On the other hand, the partition member steadily supports the analytical slide inserted therebetween. The position to be supported may be middle part and/or both sides of the analytical slide. Such a partition member may be a plate, a pair of rods, a frame or the like. The plate may be separated into two or more pieces. Height of the partition member is determined so as to hold the analytical slide inserted between the partition members. This height is not necessarily so high, and the partition members usually supports the back face of the analytical slide by its upper edge. However, the partition member may be higher, and it may support the upper edge of the analytical slide by its front face.

The partition members are provided at a slant. The inclination angle of each partition member is determined so that the analytical slide inserted between the partition members can easily be pushed out by the pushing out member and so that analytical item indication of the analytical slide arranged in the tray can easily be seen. In the case that the distance between partition members is narrow, the inclination angle of the partition member is preferably made small, i.e. more laying down. While, in the case that the distance between partition members is wide, the inclination angle is preferably made large. Every partition member inclined in the same direction. While, inclination angles of all partition members are usually equal, but this matter is not essential. Distances between them are also usually equal, but they may be different. The number of the partition members is determined according to the number of the analytical slides loaded in one cartridge. The partition members may, of course, be more than the number of the analytical slides in one cartridge. The partition members are arranged in row(s) so that the legs of the pushing out member can move both sides of or the space between the row(s) of the partition members.

The guide for sliding the pushing out member is provided on the tray. This guide may be a groove or a projection line. Cross section of the guide may be circular, square or others. The number of the guide may be one, two or more. The upper edge of the following wall members may also be utilized as the guide.

In order to secure the position of the analytical slide, a pair of wall members may preferably be provided on both sides of the row of the partition members. The wall member may be plate. Height of the wall member is near to or contact with the lower end of the side panel of the pushing out member, so that the analytical slide is smoothly lifted to transfer to the receiving part of the pushing out member. Two wall members are positioned in parallel at a distance of slightly broader than the width of the analytical slide. The wall members make the arrangement of the analytical slides on the tray easy, and the travel of the pushing out member can be guided by them.

The pushing out member slides on the tray and pushes the lower edge of the exposed position of the analytical slide out of the row of the partition members. This member should also have the functions to receive and to stack the analytical slide pushed out from the tray. Thus, the pushing out member has a sliding part, a pushing part and a receiving part.

The sliding part is provided at each position corresponding to the guide of the tray. In order to move smoothly, rollers may be provided at its sliding face (usually lower face).

The pushing part is the side face to face the analytical slide inserted between the partition members. This face may be perpendicular or inclined in the direction opposite to the analytical slide to be pushed.

The receiving part is located on the upper part, and joined to the pushing part. In order to hold the analytical slides lifted to this part, at least, the front panel (the back panel in the travelling direction), and two side panels are necessary. These panels may be plates, frames or rods. When the tray is provided with the wall members, distance between the inner faces of the side panels is preferably identical with or slightly broader than those of the wall members.

A handle member which assists the travel of the pushing out member may be attached to the pushing out member or may separately be provided. In the latter case, a sliding part is necessary to the handle member. The path for the sliding part may be the same as the path for sliding the pushing out member or may be provided independently.

Cartridge in which analytical slides are loaded may be composed of two or more parts, and a part including the main body of the cartridge may be utilized as a part or whole of the pushing out member. Besides, a part or whole of the cartridge may be attached to the terminal of the tray in order to receive the analytical element stacked in the pushing out member.

When analytical slides are loaded into a cartridge by using the apparatus of the invention, the analytical slide is first inserted into each space between the partition members of the tray to arrange in a prescribed order. Then, a pushing out member is moved toward the analytical slide. The pushing part which is the side of the pushing out member to face the analytical slide butts against the lower edge of the first analytical slide arranged on the tray, and pushes it toward the moving direction. The analytical slide moves backward, and it is lifted by the guide of the slope of the partition member. When the pushing part passes through the upper edge of the partition member, the analytical slide leaves the partition member. The pushing part butts against the lower edge of the second analytical slide, and pushes it up in the same manner as above. The second analytical side leaves the partition member, and it is stacked under the first analytical slide. At that time, it pushes the first analytical slide up into the receiving part of the pushing out member. These movements are repeated, and the analytical slides are stacked in the receiving part in the prescribed order. Then, the analytical slides are transferred to a cartridge. In the case that the pushing out member is utilized as a part or the main body of the cartridge, the pushing out member containing the analytical slides is taken out, and necessary members such as a lid are attached to use.

In the apparatus of the invention, not only since the analytical item indication of every analytical slide arranged on the tray can be seen at the arrangement working but also since the order of the analytical slides arranged on the tray can be checked after the arrangement is finished, the analytical slides can exactly be loaded in a cartridge in a prescribed order. Moreover, by using the apparatus of the invention, the analytical slides can easily and rapidly be loaded in a cartridge.

EXAMPLES

Example 1

An example of the apparatus of the invention is illustrated in FIGS. 1 to 7.

Figure 2:
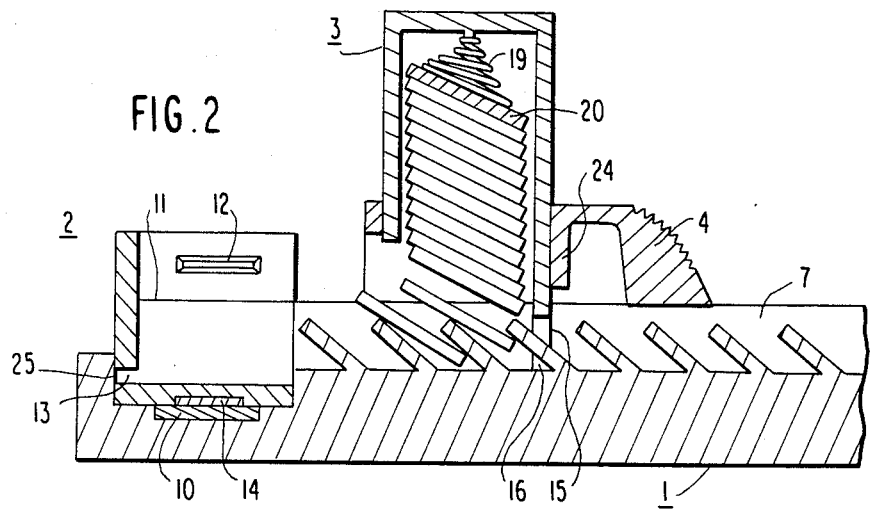
FIG. 2 is a partial sectional side view thereof.

As shown in FIG. 1 which is a partial cutaway side view, this apparatus consists of a tray 1, a cartridge bottom member 2 to be mounted at the rear end of the tray 1 in a detachable state, a cartridge upper member 3 (pushing out member) to be put on the tray 1 at its front end, and a handle 4 for pushing the cartridge upper member 3. Partition plates 5 are formed on the tray body in parallel having an inclination angle of 45 degrees toward rear direction. Every partition plate 5 has the same shape, and arranged at equal spaces in the longitudinal direction of the tray 1. As shown in FIG. 2, the height of the partition plate 5 is lower than the analytical slide 8, and the partition plate 5 supports the reverse face of the analytical slide by its upper edge.

Figure 3:
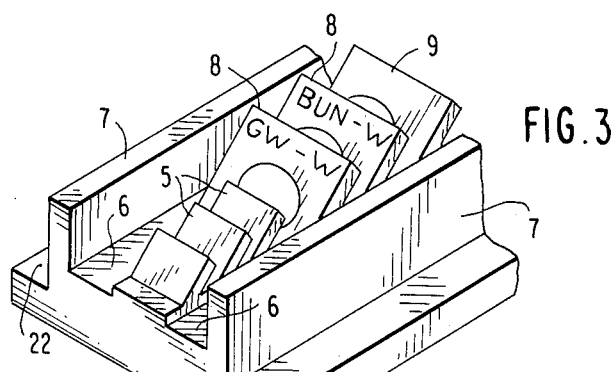
FIG. 3 is a partial perspective view of the tray of the above apparatus.

As shown in FIG. 3, each partition plate 5 is square, and arranged at the center of the tray body in a row. The width of the partition plates 5 is narrower than the width of the analytical slide 8, and both side portions of the analytical slide 8 are projected out of the row of the partition plates 5. The plate 9 is a divider dividing a set of the analytical slides 8, ..., 8 for each sample, and its size is the same as the analytical slide 8. A pair of pathes 6, 6 for sliding the cartridge upper member 3 is provided on both sides of the row of the partition plates 5. This path 6 is a shallow channel having a flat bottom. In order to secure the position of the analytical slide, a pair of wall members 7, 7 are provided out of the above pathes 6, 6. The wall member has a plate shape, and its upper edge is slightly higher than the upper edge of the partition plate 5. A pair of rails 22, 22 for the handle 4 is projected from the lower edge of each wall member 7.

As shown in FIG. 2, a recess 25 for setting the cartridge bottom member 2 is formed, and a magnet 10 for fixing the cartridge bottom member 2 is buried in the bottom.

Figure 4:
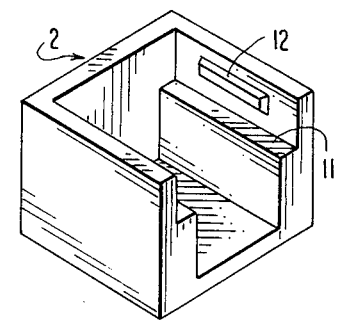
FIG. 4 is a perspective view of the cartridge bottom member of the apparatus.

The cartridge bottom member 2 has, as shown in FIGS. 2 and 4, a box shape of which the front face and the upper face are opened. A pair of steps 11, 11 are formed on both inner side faces at the same height as the upper edge of the wall member 7 when the cartridge bottom member 2 is set in the recess 25. A pair of projection lines 12, 12 are formed above the step 11. This projection lines 12 is provided in order to engage with the channel recess 18 of the cartridge upper member 3. A slit 13 is formed at the lower end of the rear face, and a magnet 14 is buried in the reverse face. The slit 13 is provided in order to insert a pushing plate (not illustrated) to push the analytical slide 8 out of the cartridge in an analyzer. The magnet 14 is attracted to the magnet 10 to fix the cartridge bottom member 2 on the tray 1.

Figure 5:
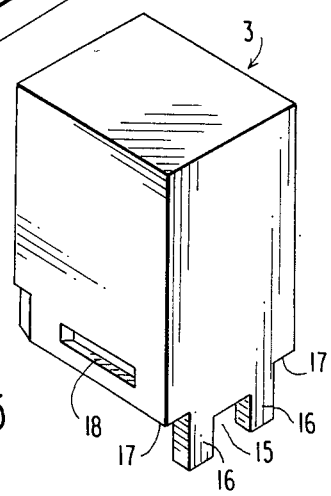
FIG. 5 is a perspective view of the cartridge upper member (pushing out member) of the apparatus.
Figure 6:
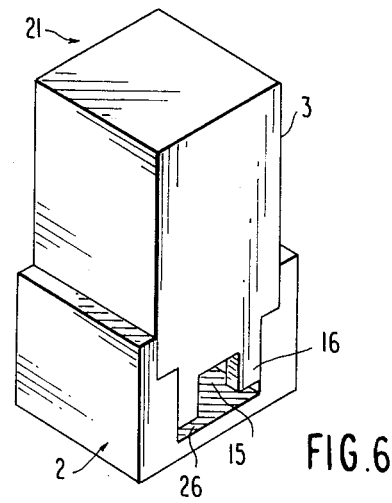
FIG. 6 is a perspective view of the cartridge composed of the above bottom member and the above upper member.
Figure 12:
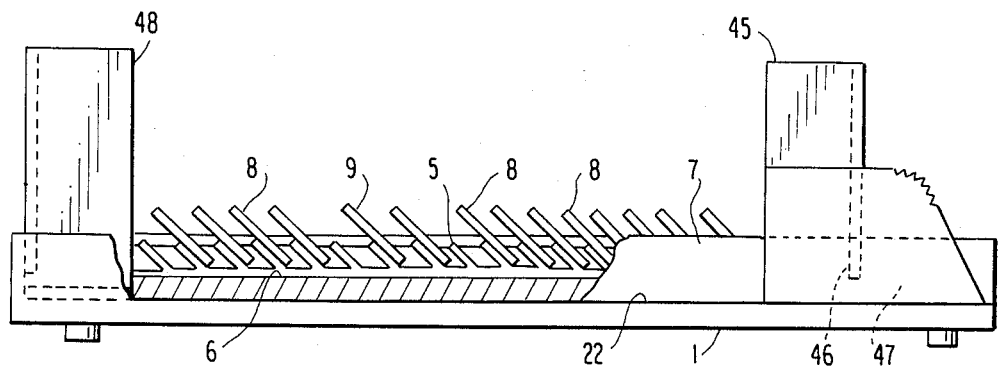
FIG. 12 is a partial cutaway side view of still another apparatus for loading analytical slides embodying the invention.

The cartridge upper member 3 has, as shown in FIGS. 2 and 5, a box shape of which the bottom face is opened, and it combines with the cartridge bottom member 2 to form a complete cartridge. A pair of sliding legs 16, 16 are elongated downward from the lower edge of the front face, and a recess 15 is formed by the sliding legs 16, 16. When the cartridge upper member 3 is put on the tray 1, the sliding legs 16, 16 slide on the pathes 6, 6 of the tray 1, and at that time, the recess 15 passes through the row of the partition plates 5, 5, ..., 5. The lower ends 17, 17 of both sides of the cartridge upper member 3 also touch and slide the upper edges of the wall members 7, 7. However, either of the sliding legs 16, 16 or the above lower ends 17, 17 may not touch, and either pair slides alone. A pair of channel recesses 18, 18 are formed on both outer side faces of the cartridge upper member 3, and a presser plate 20 is mounted on the ceiling through a spring 19. This presser plate 20 presses the analytical slides 8 and the dividers 9 stacked in the cartridge upper member 3. As shown in FIG. 6, the cartridge upper member 3 is joined to the cartridge bottom member 2. When the lower part of the cartridge upper member 3 is interposed into the front side of the cartridge bottom member 2, the lower end 17 rides on the step 11, and slides on it. Then, the projection lines 12, 12 engage with the channel recesses 18, 18 to complete a cartridge for an analyzer. A slit 26 for taking out the analytical slides 8 forms at the lower end of the front face of the cartridge.

Figure 7:
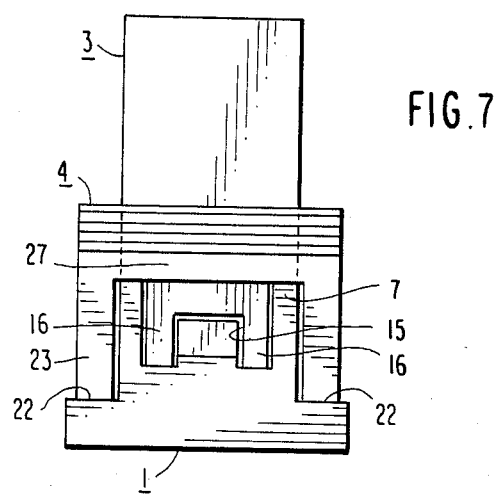
FIG. 7 is a front view of the apparatus.

The handle 4 is, as shown in FIG. 1, attached to the front of the cartridge upper member 3. As shown in FIG. 7, it is put stradding the row of the partition plates 5 and two wall members 7, and its front is a reverse U shape. This handle 4 consists a pair of sliding plates 23, 23 and its connecting part 27. The sliding plates 23, 23 have a trapezoid shape, and they slide on the rails 22, 22 of the tray 1. The front of the connecting part 27 has a slope, as shown in FIG. 2, and the upper part of the slope is knurled. The rear end 24 of the connecting part 27 is turned downward. A large recess for embracing the cartridge upper member 3 is formed by the connecting part 27 and the sliding plates 23, 23.

As the use of this apparatus, the cartridge bottom member 2 is set into the recess 25 of the tray 1, and the cartridge upper member 3 and the handle 4 are put on the front end of the tray 1. The analytical slides 8 and the dividers 9 are inserted into each space between the partition plates 5, 5 in a prescribed order. This arrangement may be carried out prior to the setting of the cartridge bottom member 2, etc. Then, the handle 4 is pushed toward the rear end of the tray 1, and the cartridge upper member 3 travels together with the handle 4. The rears of the sliding legs 16, 16 butt against the lower edge of the first analytical slide 8, and push it. The analytical slide 8 moves backward, and it is lifted by the guide of the slope of the partition plate 5. When the rear of the sliding leg 16 passes through the upper edge of the partition plate 5, the analytical slide 8 leaves the partition plate 5. The sliding legs 16, 16 butt against the second analytical slide 8, and push it up in the same manner as above. The second analytical slide 8 leaves the partition plate 5, and stacked under the first analytical slide 8. At that time, it pushes the first analytical slide 8 up into the cartridge upper member 3. These movements are repeated, and the analytical slides 8 and the dividers 9 are stacked in the cartridge upper member 3 in the prescribed order. After all analytical slides 8 and dividers 9 arranged on the tray 1 are taken in the cartridge upper member 3, the cartridge upper member 3 is further pushed to travel toward the rear end of the tray 1. The cartridge upper member 3 reaches the cartridge bottom member 2, and the lower ends 17, 17 ride on the steps 11, 11. The lower ends 17, 17 slide on them, and the projection lines 12, 12 engage with the channel recesses 18, 18. The cartridge thus joined, containing the analytical slides 8 and the dividers 9 stacked in the prescribed order, is detached from the tray 1, and loaded in the slide supplying part of an analyzer.

EXAMPLE 2

Another example of the apparatus of the invention is illustrated in FIGS. 8 to 11.

Figure 9:
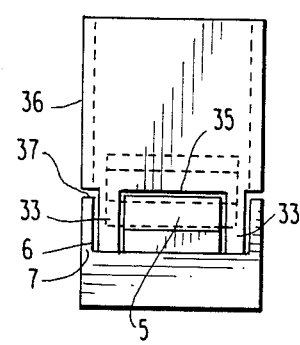
FIG. 9 is a front view thereof.
Figure 8:
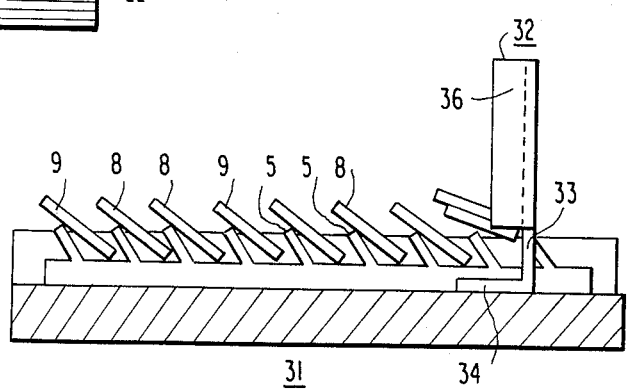
FIG. 8 is a sectional side view of another apparatus for loading analytical slides embodying the invention.

As shown in FIGS. 8 and 9, this apparatus consists of a tray 31 and a fork member 32.

The tray 31 is similar to the tray 1 of Example 1, and partition plates 5, 5, ..., 5 are provided in a row on the tray body in an inclination state. A pair of pathes 6, 6 are formed on both sides of the row, and a pair of wall members 7, 7 are provided out of the pathes 6, 6. However, the rails 22, 22 and the recess 25 are not provided.

Upper part of the fork member 32 consists of a front panel and two short side panels 36, 36. This part embraces the stack of the analytical slides 8 and the dividers 9. A pair of legs 33, 33 are elongated downward from the lower edge of the front panel, and their ends are turned toward the rear of the tray 31 to form a pair of forks 34, 34. A recess 35 for passing through the row of the partition plates 5 is formed by the legs 33, 33, 37 and the lower end of the front panel, and the lower end of the side panel 36 slides on the upper edge of the wall member 7.

Figure 10:
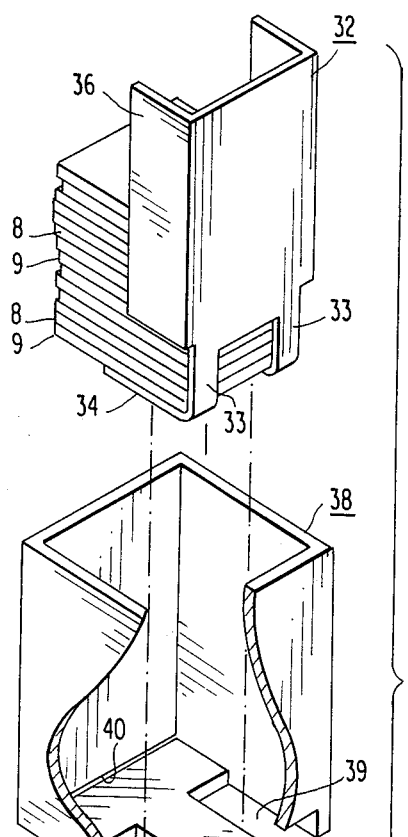
FIG. 10 is a partial cutaway perspective view indicating loading state of analytical slides into the cartridge of this apparatus.

The cartridge 38 for this apparatus is illustrated in FIG. 10. This cartridge 38 has a box shape of which the upper face is opened. In order to draw out the fork member 32, a U shape hole having a narrow connecting part is bored through the bottom. A pair of slits 40, 41 are formed at each lower end of the front face and the rear face. The slit 40 of the rear face is provided for insertion of a pushing plate 42, and the other slit 41 is provided as the taking out opening of the analytical slide 8.

Figure 11:
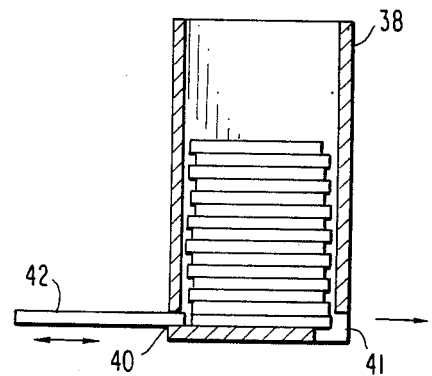
FIG. 11 is a sectional side view of the cartridge loaded with analytical slides.

At the time of loading the analytical slide 8, the analytical slides 8 and the dividers 9 are inserted into each space between the partition plates 5, 5 in a prescribed order. Then, the fork member 32 is put on the front end of the tray 31, and pushed to travel toward the rear end of the tray 31. During travelling, the analytical slides 8 and the dividers 9 are stacked in the upper part of the fork member 32 in the same mechanism as in the case of Example 1. When the fork member 32 reaches the rear end of the tray 31, all analytical slides 8 and dividers 9 are stacked in the fork member 32. The fork member 32 is taken up, and at that time, the forks 34, 34 support this stack as shown in FIG. 10. Then, the fork member 32 holding the stack is inserted into the cartridge 38, and the fork member 32 is further drawn out of the cartridge 38 from its bottom through the U shape hole 39. Thus, the analytical slides 8 and the dividers 9 are loaded in the cartridge 38 in the prescribed order. The cartridge 38 is loaded in the slide supplying part of an analyzer, and the analytical slide 8 is taken out one piece by one piece as shown in FIG. 11.

EXAMPLE 3

Still another example of the apparatus of the invention is illustrated in FIGS. 12 to 15.

This apparatus is a modification of the apparatus of Example 1, and the tray 1 is the same as Example 1.

Figure 14:
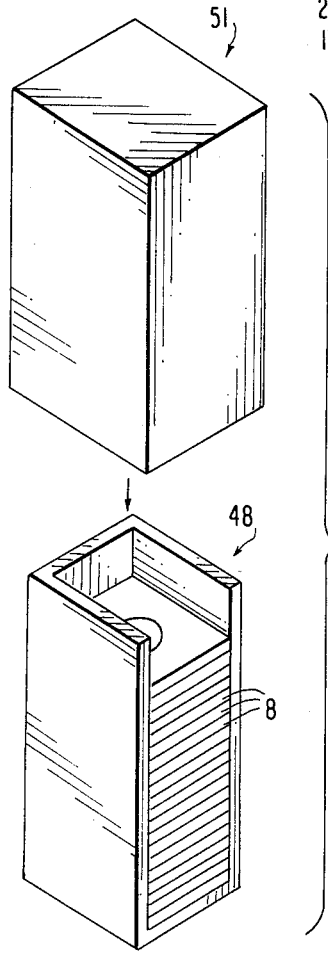
FIG. 14 is an exploded view of the cartridge of this apparatus.

Instead of the cartridge bottom member 2, a cartridge body 48 is employed. This cartridge body 48 has, as shown in FIG. 14, a box shape of which the front face and the upper face are opened. The steps 11, 11 and projection lines 12, 12 are not formed, while the slit 13 and the magnet 14 are provided. The pushing out member 45 is similar to Example 1. Compared to Example 1, the ceiling together with the presser plate 20 and the rear panel are not provided, and the handle 4 is integrally provided. Other parts are similar to Example 1. That is, the front panel, the sliding legs 46, 46 corresponding to 16, 16, two side panels of which the lower ends slide on the wall member 7, 7, a pair of sliding plates and its connection part are provided. The upper part of the connecting part is knurled, whereas the channel recesses 18, 18 of the side panels are not formed. The pushing out member 45 is not used as a part of the cartridge, but a long cover 51 shown in FIG. 14 is used as a part of the cartridge.

Figure 13:
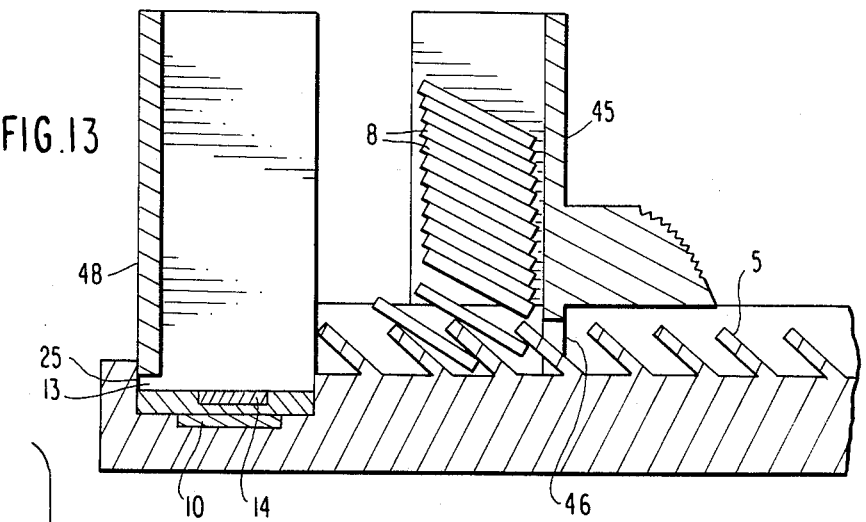
FIG. 13 is a partial sectional view thereof.
Figure 15:
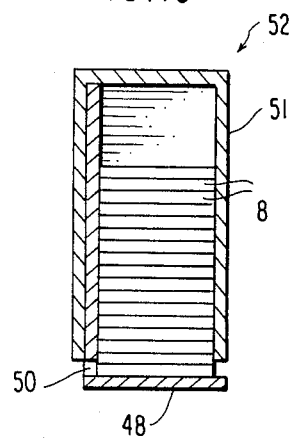
FIG. 15 is a sectional side view of the cartridge.

At the time of the loading, the analytical slides 8 and the divider 9 are inserted into each space between the partition plates 5, 5 in a prescribed order. Then, the pushing out member 45 is pushed to travel toward the rear end of the tray 1. During travelling, the analytical slides 8 and the dividers 9 are stacked in the pushing out member 45 as shown in FIG. 13, and the pushing out member 45 takes the stack on the cartridge body 48 at the rear end of the tray 1. The cartridge body 48 is detached from the tray 1, and the cover 51 is put on it as shown in FIG. 15. This cartridge thus completed is loaded in the slide supplying part of an analyzer.

I claim:

1. An apparatus for loading analytical slides in a cartridge comprising
a tray having a plurality of spaced apart, upwardly inclined partition members disposed in a row with each partition member having a width narrower than the width of analytical slides adapted to be disposed in the tray between the partition members and
a pushing out member having slide receiving means slidably mounted on said tray for movement along said tray in the direction said partition members are inclined and having slide engaging means disposed adjacent said row of partition members for engaging each slide as the pushing out member moves along said tray to push each slide upwardly into said slide receiving means to form a stack of slides therein.

2. The apparatus as set forth in claim 1, wherein the height of each partition member is lower than the height of said analytical slides.

3. The apparatus according to claim 1, further comprising a pair of wall members provided on opposite sides of said row of partition members in spaced relation thereto to define a pair of pathes and wherein said slide engaging means is comprised of pair of downwardly extending projections on said slide receiving means disposed between said partition members and said wall members for movement along said pathes.

4. The apparatus according to claim 1, wherein said slide receiving means is comprised of a front panel and two side panels extending upwardly from said slide engaging member.

5. The apparatus according claim 4, further comprising a pair of wall members disposed in spaced apart relation on opposite sides of said row of partition members and wherein lower ends of said side panels are disposed adjacent upper edges of said wall members.

6. The apparatus according to claim 1, further comprising handle means for pushing said pushing out member along said tray.

7. The apparatus according to claim 1, wherein said cartridge is comprised of an upper member and a bottom member, means for detachably mounting said bottom member on said tray adjacent the end of the row of partition members, said upper member of said cartridge constituting said pushing out member and slide receiving means and including sliding means detachably supporting said upper member of said cartridge for sliding movement along said tray into mating engagement with said bottom member of said cartridge.

8. The apparatus according to claim 1, wherein said cartridge is comprised of three-sided rectilinear member having a bottom wall detachably secured on said tray adjacent one end of said row of partition members and having an open side facing said row for receiving a stack of slides from said slide receiving means.

9. The apparatus according to claim 8 further comprising a cover member adapted to close the top and open side of said cartridge.

10. The apparatus according to claim 1, wherein said slide receiving means is comprised of a transverse, vertically extending wall having a pair of side walls disposed in the direction of said row of partition members and said slide engaging means is comprised of a pair of downwardly depending L-shaped members disposed on opposite sides of said row of partition members for engaging said slides as said L-shaped members slide along said tray.

11. The apparatus according to claim 10, wherein said cartridge is comprised of a rectilinear box-like structure having an open top into which said slide receiving means having a stack of slides therein may be inserted, said box having a bottom with apertures corresponding to said L-shaped members for permitting said slide receiving means to pass through the bottom of said box while leaving the stack of slides within said box.

12. An apparatus for loading analytical slides in a cartridge comprising
a tray having a plurality of spaced apart, upwardly inclined partition members disposed in rows with each partition member having a width narrower than the width of analytical slides adapted to be disposed in the tray between the partition members in each row and a pushing member having slide receiving means slidably mounted on said tray for movement along said tray in the direction said partition members are inclined and having slide engaging means disposed adjacent said rows of partition members for engaging each slide as the pushing out member moves along said tray to push each slide upwardly into said slide receiving means.

13. An apparatus according to claim 12, wherein said slide engaging means engages each slide so that the slide is supported in the middle part thereof.

* * * * *